United States Patent [19]
West et al.

[11] Patent Number: 5,840,787
[45] Date of Patent: Nov. 24, 1998

[54] CELLULOSIC PRODUCTS USING HIGH-BULK CELLULOSIC FIBERS

[75] Inventors: Hugh West; Amar N. Neogi, both of Seattle; Dwight Albert Dudley, II, Federal Way; Dwayne M. Shearer, Seattle, all of Wash.

[73] Assignee: Weyerhaeuser Company, Tacoma, Wash.

[21] Appl. No.: 723,325

[22] Filed: Sep. 30, 1996

Related U.S. Application Data

[63] Continuation-in-part of Ser. No. 218,106, Mar. 25, 1994, abandoned.

[51] Int. Cl.$^6$ .................................. C08L 1/02; D21J 1/00
[52] U.S. Cl. ................................ 524/35; 524/13; 524/14; 106/163.1; 106/210; 162/157.6
[58] Field of Search ............................... 524/13, 14, 15, 524/16, 35; 525/54.21; 106/163.1, 210; 1692/157.6

[56] References Cited

U.S. PATENT DOCUMENTS

| | | | |
|---|---|---|---|
| 3,395,708 | 8/1968 | Hervey et al. | 128/284 |
| 3,440,135 | 4/1969 | Chung | 162/157 |
| 3,554,862 | 1/1971 | Hervey et al. | 162/158 |
| 3,658,613 | 4/1972 | Steiger | 156/153 |
| 3,677,886 | 7/1972 | Forsblad et al. | 162/72 |
| 3,819,470 | 6/1974 | Shaw et al. | 162/157 C |
| 4,035,147 | 7/1977 | Sangenis et al. | 8/116.4 |
| 4,124,439 | 11/1978 | Dessauer | 162/146 |
| 4,144,122 | 3/1979 | Emanuelsson et al. | 162/158 |
| 4,303,471 | 12/1981 | Laursen | 162/158 |
| 4,351,699 | 9/1982 | Osborn, III | 162/112 |
| 4,476,323 | 10/1984 | Hellsten et al. | 564/294 |
| 4,822,453 | 4/1989 | Dean et al. | 162/187 |
| 4,853,086 | 8/1989 | Graef | 162/157.6 |
| 4,889,595 | 12/1989 | Herron et al. | 162/157.6 |
| 4,889,597 | 12/1989 | Bourbon et al. | 162/157.6 |
| 4,913,773 | 4/1990 | Knudson et al. | 162/129 |
| 4,935,022 | 6/1990 | Lash et al. | 604/368 |
| 5,055,247 | 10/1991 | Veda et al. | 524/13 |
| 5,137,537 | 8/1992 | Herron et al. | 162/157.6 |
| 5,217,445 | 6/1993 | Young et al. | 604/381 |
| 5,225,047 | 7/1993 | Graef et al. | 162/9 |
| 5,308,876 | 5/1994 | Hansen et al. | 524/13 |
| 5,308,896 | 5/1994 | Hansen et al. | 524/13 |

FOREIGN PATENT DOCUMENTS

| | | |
|---|---|---|
| 0 440 472 A1 | 1/1991 | European Pat. Off. |
| 0440472 | 1/1991 | European Pat. Off. |
| 0 429 112 | 5/1991 | European Pat. Off. |
| 0429112 | 5/1991 | European Pat. Off. |
| 2234422 | 6/1974 | France. |

OTHER PUBLICATIONS

*HBA*, Weyerhaeuser Company, 1990.
Blanchard, Eugene J., Robert M. Reinhardt, Elena E. Graves and B. A. Kottes Andrews. Dyeable durable press cottons finished with citric acid and nitrogenous additives, International Conference, American Association of Textile Chemists and Colorists (1992).
Blanchard, Eugene J., Robert M. Reinhardt, Elena E. Graves, and B. A. Kottes Andrews. Dyeable cross–linked cellulose from low formaldehyde and non–formaldehyde finishing system. *Industrial and Engineering Chemistry*, 33 (4): 1030–1034 (1994).
Carter, M.E. Chemical modification via crosslinking reactions. *Essential Fiber Chemistry*, pp. 8–18, Marcel Dekker, New York (1991).
Carter, M.E. Dyeing. *Essential Fiber Chemistry* pp. 18–21, Marcel Dekker, New York (1991).
HBA—Weyerhaeuser Paper Company Introduces High Bulk Additive. Brochure available from Weyerhaeuser Company, Tacoma, Washington (1990).
"Dyeable Durable Press Cottons Finished with Citric Acid and Nigrogenous Additives," Blanchard, Eugene J., Robert M. Reinhardt, Elena E. Graves and B.A. Kottes Andrews.
"Dyeable Cross–Linked Cellulose from Low Formaldehyde and Non–Formaldehyde Finishing Systems," Blanchard, Eugene J., Robert M. Reinhardt, Elena E. Graves and B.A. Kottes Andrews; Published 1994 by the American Chemical Society.
"Chemical Modification via Crosslinking Reactions," *Essential Fiber Chemistry Carter*, M.E. and Marcel Dekker, 1971.
"Other Finished Treatments," *Essential Fiber Chemistry*, Carter, M.E. and Marcel Dekker, 1971.

*Primary Examiner*—Peter A. Szekely

[57] ABSTRACT

A fiber/binding agent composition comprising: individualized chemically crosslinked high-bulk fibers comprising individualized fibers chemically intra-fiber crosslinked with a crosslinking agent that is a polycarboxylic acid or is selected from the group of urea derivatives consisting of methylated urea, methylated cyclic ureas, methylated lower alkyl substituted ureas, dihydroxy cyclic ureas, and methylated dihydroxy cyclic ureas, and mixtures thereof; and from about 0.1 to about 6 weight percent of a water-borne binding agent. The water-borne binding agent is selected from the group consisting of starch, a polyvinyl alcohol, a polyvinyl acetate latex, a polyethylene/acrylic acid copolymer, an acrylic acid polymer, an oxidized polyethylene, a polyvinyl chloride, a polyvinyl chloride/acrylic acid copolymer, an acrylonitrile/butadiene/styrene copolymer and polyacrylonitrile.

11 Claims, 9 Drawing Sheets

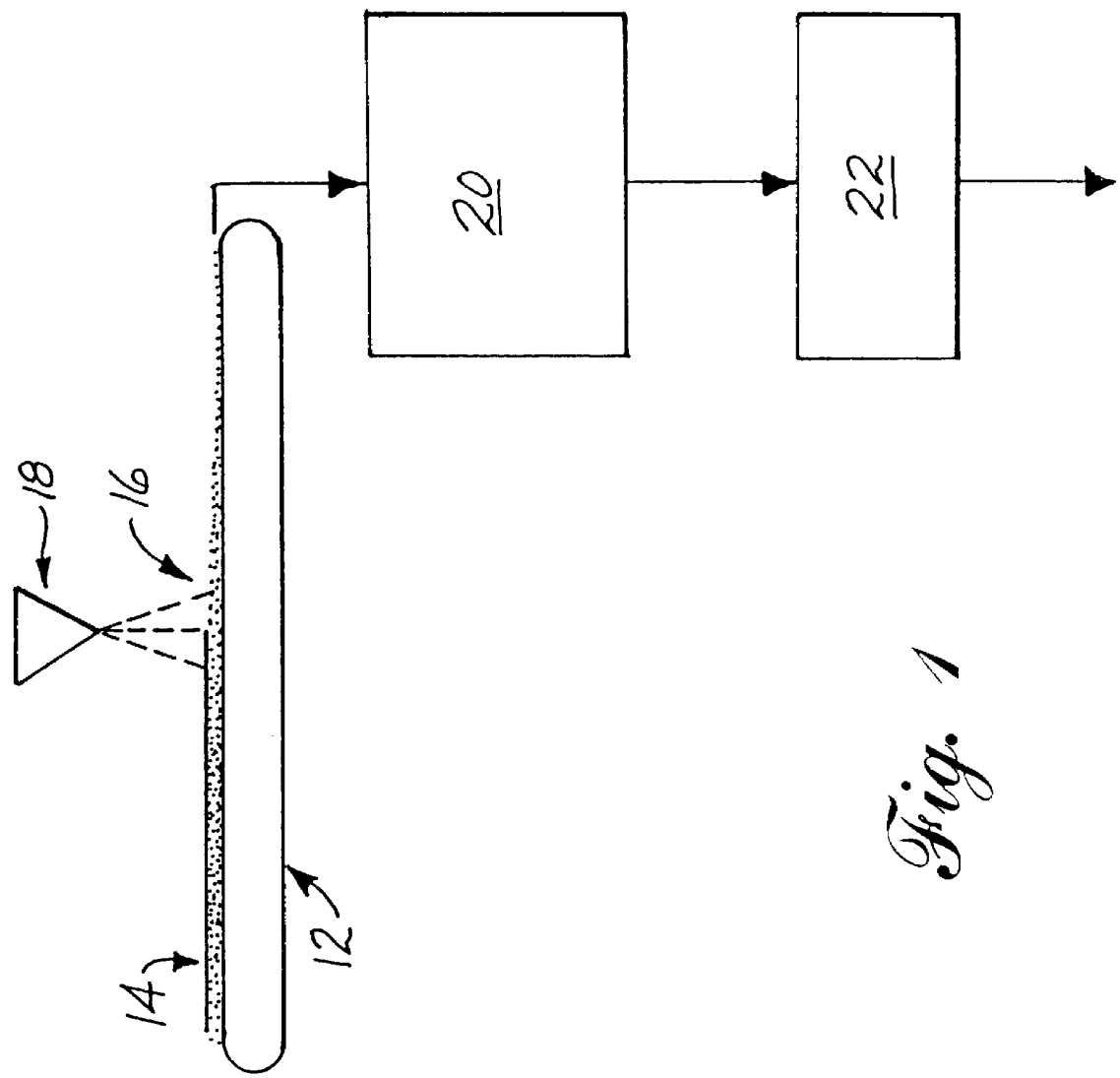

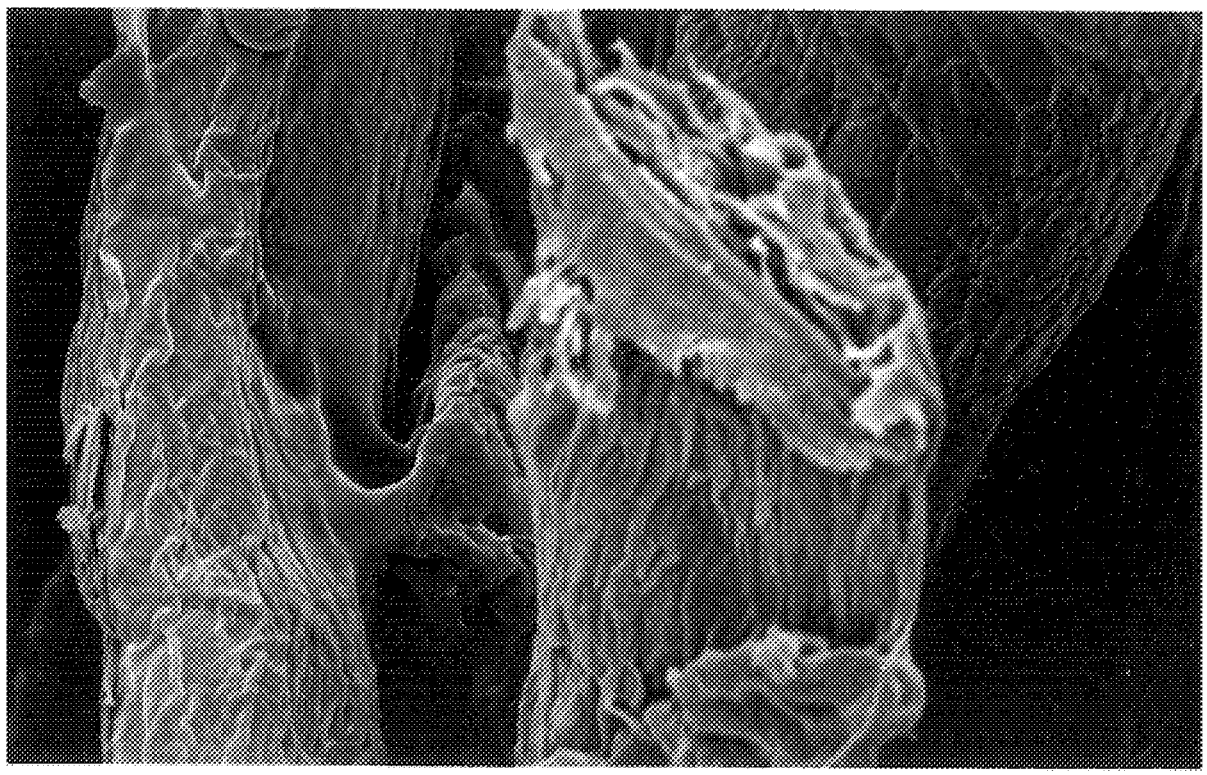
Fig. 2  20.0 μm

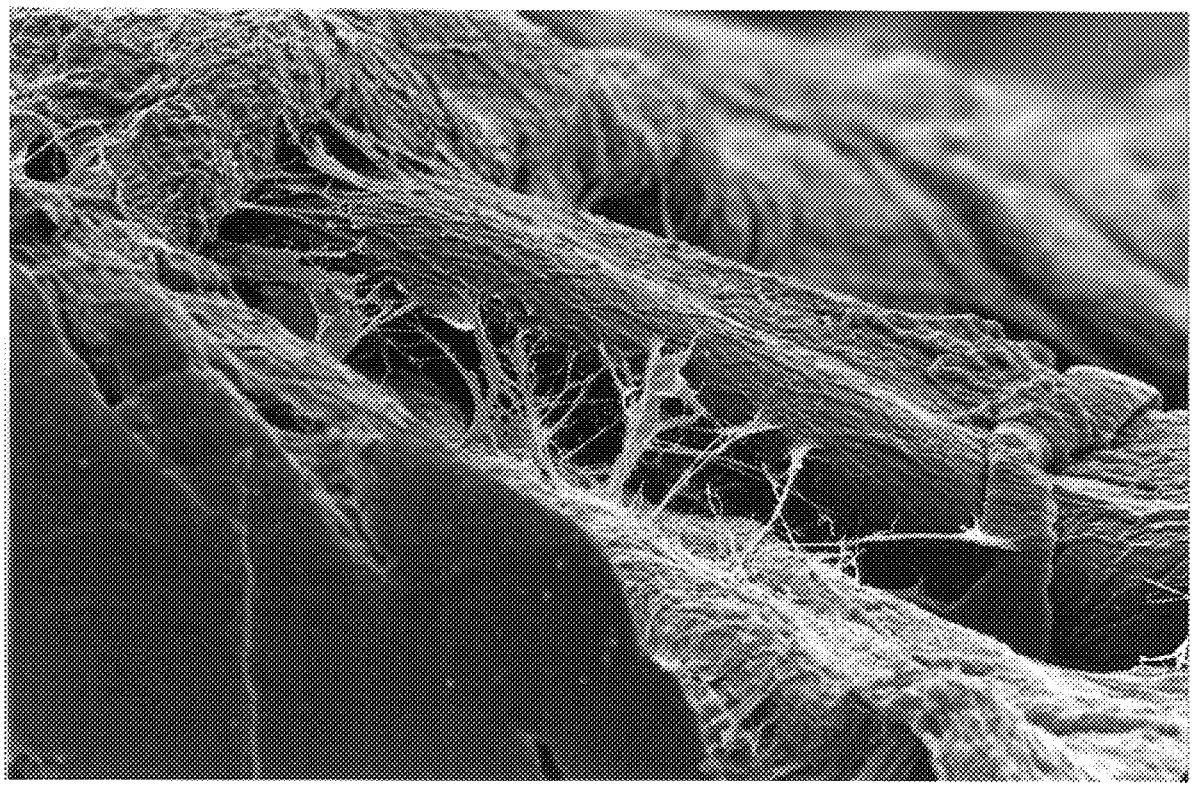
Fig. 6  ⊢——————⊣ 20.0 µm

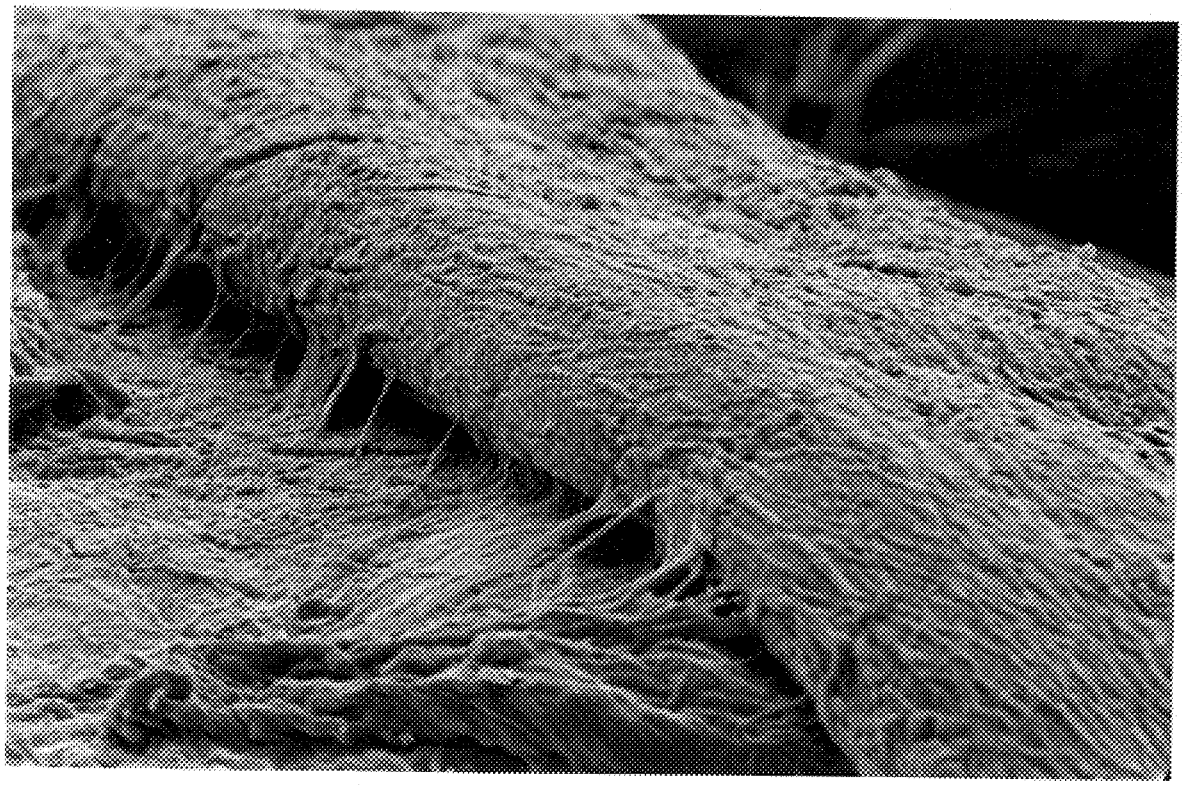
Fig.7  ⊢──────⊣ 10.0 μm

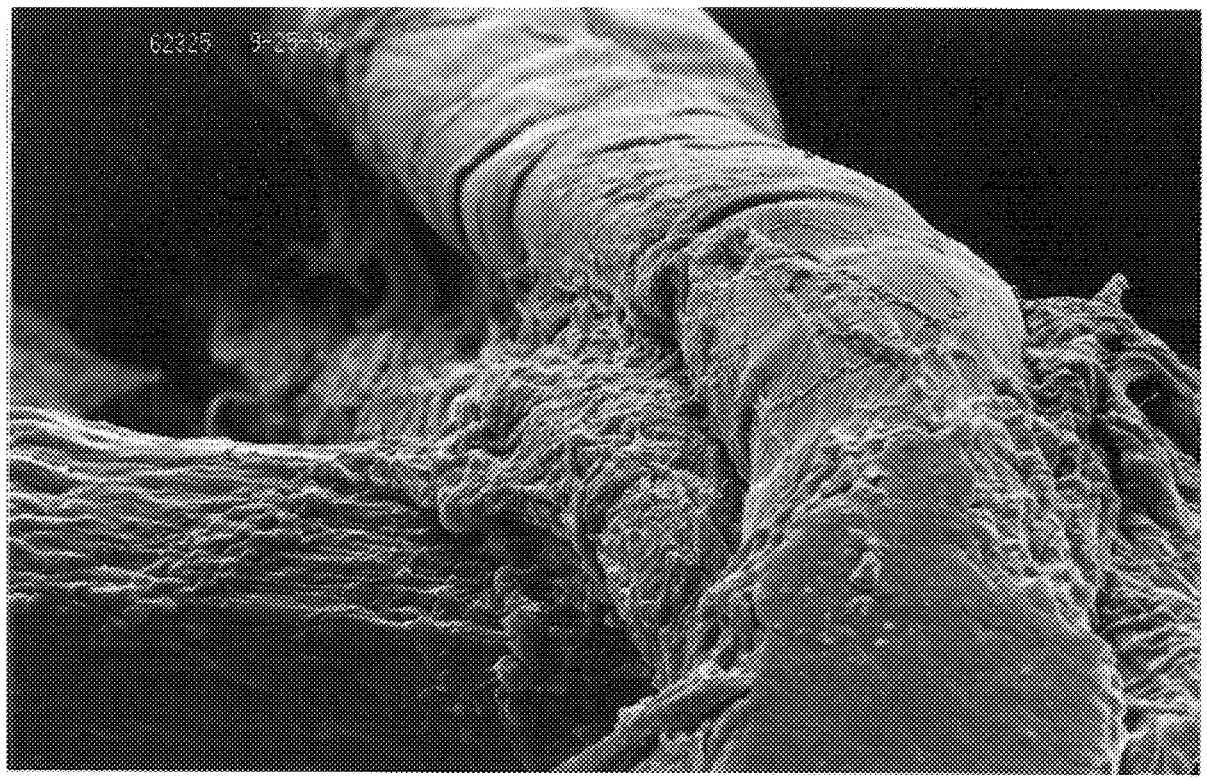
Fig. 8        |—————————————| 10.0 μm

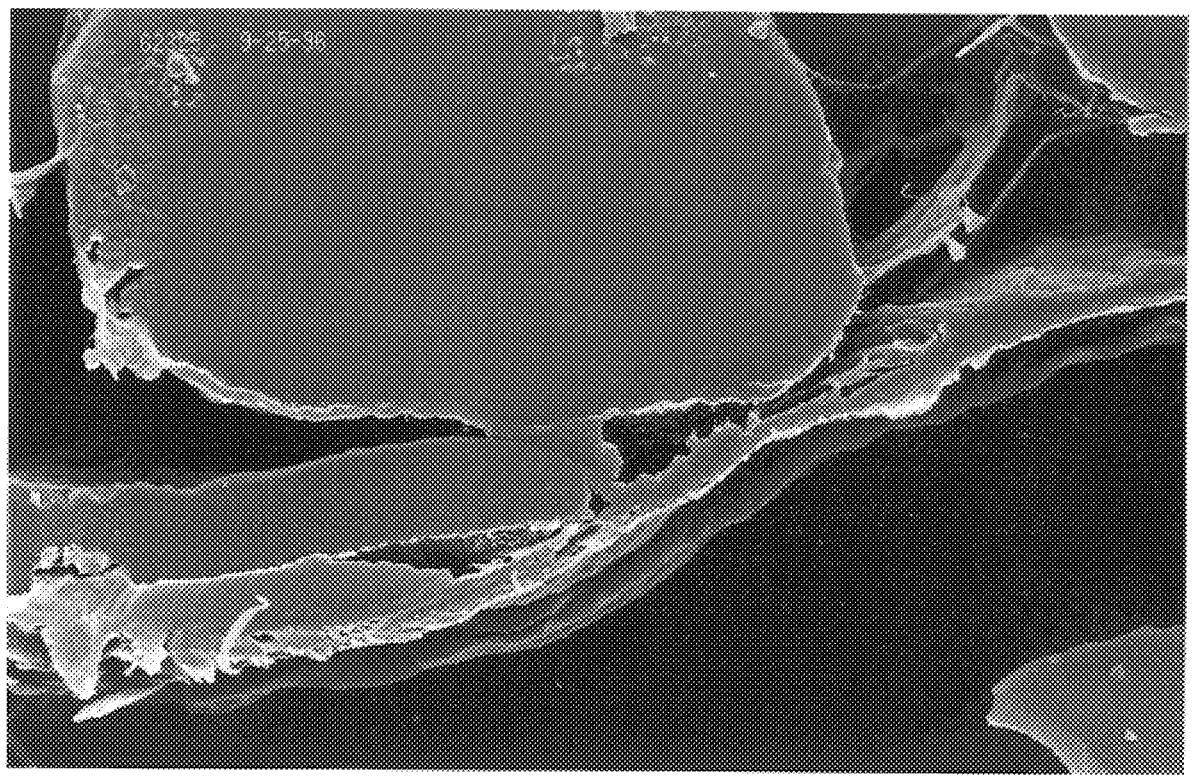
Fig. 9  |———————| 10.0 µm

CELLULOSIC PRODUCTS USING HIGH-BULK CELLULOSIC FIBERS

This application is a continuation-in-part of Ser. No. 08/218,106, filed Mar. 25, 1994, now abandoned.

FIELD OF THE INVENTION

This invention concerns cellulosic products and a method for making such products using a composition comprising chemically crosslinked cellulosic fiber and water-borne binding agents.

BACKGROUND OF THE INVENTION

Expanded polystyrene has a low density and relatively high physical strength. It is easily molded into shapes and has good insulating properties. It is used, for example, for hot drink cups and for food packages such as egg cartons and fast food containers. Unfortunately, it is not biodegradable and consumes non-renewable resources in its production.

Products made from cellulosic fibers are an attractive alternative because they are biodegradable, are made from a renewable resource and can be recycled. The main drawback is that the typical cellulosic product has a relatively high density or low bulk. Bulk is the reciprocal of density and is the volume occupied by a specific weight of material and is designated in $cm^3/gm$. The amount of cellulosic material required to provide the requisite strength creates a heavy product. It has poor heat insulating qualities.

A 1990 brochure from Weyerhaeuser Company described a chemically crosslinked cellulosic fiber known as High Bulk Additive or HBA and uses of HBA in filter paper, saturation papers, tissue and toweling, paperboard, paper and absorbent products. The brochure indicated the HBA fibers may be incorporated into paperboard at levels of 5% and 15%. The brochure also indicates that HBA can be used in the center ply of a three-ply paperboard. The board was compared with a conventional three-ply board. The basis weight was reduced 25%; the Taber Stiffness remained constant; but the breaking load was reduced from 25 kN/m to 16 kN/m in the machine direction and from 9 kN/m to 6 kN/m in the cross direction.

Knudsen et al U.S. Pat. No. 4,913,773 describe a product that has increased stiffness without an increase in basis weight. They propose a three-ply paperboard mat having an interior ply of anfractuous fibers between two exterior plies of conventional fibers. This structure, containing a middle ply of all anfractuous fibers, is compared with single ply mats of conventional and anfractuous fibers and double and triple ply constructions of different conventional fibers. Knudsen et al require at least 10% by weight of anfractuous fibers in the center ply in order to obtain the necessary stiffness. Knudsen et al does disclose a single ply control panel made from anfractuous fibers.

Knudsen et al obtain the anfractuous fibers by mechanical treatment, by chemical treatment with ammonia or caustic or by a combination of mechanical and chemical treatment. Knudsen et al may use bonding agents with certain multiply constructions. Knudsen et al discloses the addition of 1% starch to a 100% treated fiber to obtain a multi-ply paperboard with adequate bonding. Knudsen also discloses an number of bonding agents in the first full paragraph of column 5.

Kokko European Patent No. 0 440 472 discusses high-bulk fibers. The fibers are made by chemically crosslinking wood pulp using polycarboxylic acids. Kokko is directed to an individualized crosslinked fiber and high bulk and absorbent paper products made from this fiber.

Kokko used a blend of 75% untreated fibers and 25% treated fibers. The maximum dry bulk achieved by Kokko was 5.2 $cm^3/gm$ using 25% citric acid treated fibers and 5.5 $cm^3/gm$ using 25% citric acid/monosodium phosphate treated fibers.

Kokko also states that polycarboxylic acid crosslinked fibers should be more receptive to cationic additives, such as cationic strength resin, important to papermaking and that the strength of sheets made from the crosslinked fibers should be recoverable without compromising the bulk enhancement by incorporation of a cationic wet strength resin. There is no indication that Kokko actually tried cationic strength additives, or any other strength additives, with the crosslinked fibers. Consequently, Kokko did not describe the amount of cationic additive that might be used. Treating anionic fibers, such as Kokko describes, with a cationic additive substantially completely coats the entire surface of the fiber with additive. This is noted by Kokko in the experiment with methylene blue dye. The cationic additive is attracted to the entire surface of the anionic fiber. More additive is used than is needed to provide binder at the fiber-to-fiber contact points because the entire fiber is coated.

Young et al U.S. Pat. No. 5,217,445 discloses an acquisition/distribution zone of a diaper. It comprises 50 to 100% by weight of chemically stiffened cellulosic fibers and 0 to 50% by weight of a binding means. The binding means may be other nonstiffened cellulosic material, synthetic fibers, chemical additives and thermoplastic fibers. The material has a dry density less than about 0.30 $gm/cm^3$, a bulk of 3.33 $cm^3/gm$.

SUMMARY OF THE INVENTION

A need exists for new cellulosic products that have both high bulk and strength characteristics that enable such products to resemble molded plastics. Such products should have a bulk of greater than 5 $cm^3/gm$. It would also be preferable if the product could be made using high bulk fibers that are not necessarily anionic, and a binding agent that can be selected from various water-soluble or water-dispersible binding agents rather than being limited to cationic binding agents.

The present invention provides a high-bulk fiber/water-borne binding agent composition. The high-bulk fiber is an intra-fiber chemically crosslinked cellulosic material that has a bulk of from about 1 $cm^3/gm$ to about 40 $cm^3/gm$. The bulk of such fibers typically is greater than about 5 $cm^3/gm$. Suitable crosslinking agents are generally of the bifunctional type which are capable of bonding with the hydroxyl groups to create covalently bonded bridges between hydroxyl groups on the cellulose molecules within the fiber. The use of a polycarboxylic acid crosslinking agent, such as citric acid, produces a product that is especially suitable for food packaging.

Adding certain weight percents of water-borne binding agents, such as starch and polyvinyl alcohol, to chemically crosslinked high-bulk fiber produces a composition having physical characteristics superior to high-bulk fibers alone, conventional fibers alone or mixtures of high-bulk fibers and conventional fibers without such binding agents. The material has the desired strength and high bulk of expanded polystyrene. It also produces a material that requires less fiber, compared to conventional fiber, to produce the internal strength. Adjacent fibers are in contact and form plural fiber crossover points. Quite unexpectedly, the binding agent has been found to be significantly more heavily concentrated at the fiber—fiber crossover points of individual crosslinked fibers with each other and with other fibers rather than being uniformly distributed over the fiber surfaces. By having the binder so localized it much more effectively contributes strength and integrity to the mat or pad-like structure. The crosslinked high bulk fibers may be mixed with conventional uncrosslinked cellulose fibers in amounts varying from 0.5–100% by weight of the high bulk material. Preferably at least about 5% of the high bulk material should be present and more preferably at least about 10% high bulk crosslinked fibers should be used. The high bulk fibers may be individualized prior to use in forming the sheet or pad-like structures.

BRIEF DESCRIPTION OF THE DRAWINGS

FIG. 1 is a block diagram showing a process for making high-bulk chemically crosslinked fibers.

FIG. 2 is a scanning electron micrograph (SEM) of a High Bulk Additive (HBA) fiber/water-borne binding agent composition made according to this invention.

FIG. 6 shows a scanning electron micrograph (SEM) of a sheet made with refined conventional Douglas-fir kraft fiber with no starch added.

FIG. 7 is a SEM of a similar Douglas-fir sheet with added starch.

FIG. 8 is a SEM of the crossover area of a high bulk fiber and conventional Douglas-fir fiber of Sample No. 4 of Table IV.

FIG. 9 is a similar SEM showing the fibers in partial cross section.

DETAILED DESCRIPTION OF THE PREFERRED EMBODIMENTS

Figure 3A:
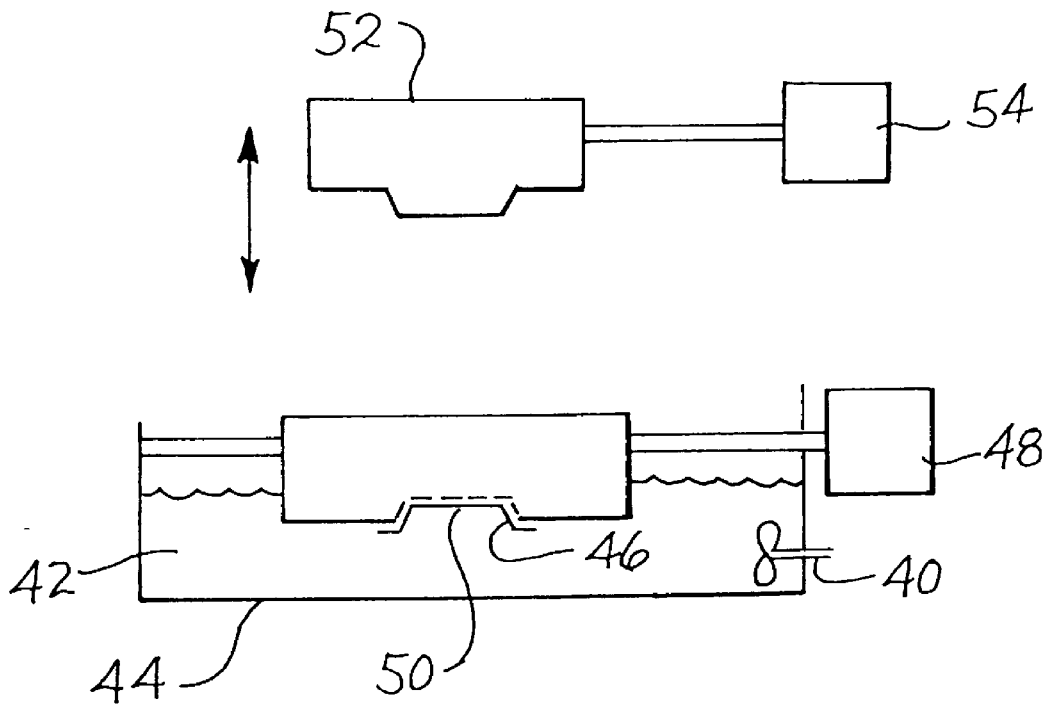
FIGS. 3A and 3B are diagrams of a plate making apparatus.

The present invention provides a composition comprising chemically crosslinked cellulosic fiber and water-borne binding agents. It is combined with conventional papermaking fiber furnish in amounts from 0.5% to 99% by weight of the total weight of the air dry furnish. Conventional papermaking fiber furnish refers to papermaking fibers made from any species, including hardwoods and softwoods, and to fibers that may have had a debonder applied to them but that are not otherwise chemically treated following the pulping process.

The cellulose fiber may be obtained from any source, including cotton, hemp, grasses, cane, husks, cornstalks or other suitable source. Chemical wood pulp is the preferred cellulose fiber.

The high-bulk chemically crosslinked cellulosic fibers is an intra-fiber crosslinked cellulosic fiber which may be crosslinked using a variety of suitable crosslinking agents. The individual fibers are each comprised of multiple cellulose molecules and at least a portion of the hydroxyl groups on the cellulose molecules have been bonded to other hydroxyl groups on cellulose molecules in the same fiber by crosslinking reactions with the crosslinking agents. The crosslinked fiber may be formed into a mat having a bulk of from about 1 $cm^3$/gm to about 50 $cm^3$/gm, typically from about 10 $cm^3$/gm to about 30 $cm^3$/gm, and usually from about 15 $cm^3$/gm to about 25 $cm^3$/gm.

The crosslinking agent is a liquid solution of any of a variety of crosslinking solutes known in the art. Suitable crosslinking agents are generally of the bifunctional type which are capable of bonding with the hydroxyl groups and create covalently bonded bridges between hydroxyl groups on the cellulose molecules within the fiber. Preferred types of crosslinking agents are selected from urea derivatives such as metholylated urea, methylolated cyclic ureas, methylolated lower alkyl substituted cyclic ureas, methylolated dihydroxy cyclic ureas. Preferred urea derivative crosslinking agents are dimethyloldihydroxyethylene urea (DMDHEU) and dimethyldihdroxyethylene urea. Mixtures of the urea derivatives may also be used. Preferred polycarboxylic acid crosslinking agents are citric acid, tartaric acid, malic acid, succinic acid, glutaric acid and citraconic acid. These polycarboxylic crosslinking agents are particularly useful when the proposed use of the material is food packaging. Other polycarboxylic crosslinking agents that may be used are poly(acrylic acid), poly(methacrylic acid), poly(maleic acid), poly(methylvinylether-co-maleate) copolymer, poly(methylvinylether-co-itaconate) copolymer, maleic acid, itaconic acid, and tartrate monosuccinic acid. Mixtures of the polycarboxylic acids may also be used.

Other crosslinking agents are described in Chung U.S. Pat. No. 3,440,135, Lash et al U.S. Pat. No. 4,935,022, Herron et al U.S. Pat. No. 4,889,595, Shaw et al U.S. Pat. No. 3,819,470, Steijer et al U.S. Pat. No. 3,658,613, Dean et al U.S. Pat. No. 4,822,453, and Graef et al U.S. Pat. No. 4,853,086, all of which are in their entirety incorporated herein by reference.

The crosslinking agent can include a catalyst to accelerate the bonding reaction between the crosslinking agent and the cellulose molecule, but most crosslinking agents do not require a catalyst. Suitable catalysts include acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus containing acids may also be used.

The crosslinking agent typically is applied in an amount ranging from about 2 kg to about 200 kg chemical per ton of cellulose fiber and preferably about 20 kg to about 100 kg chemical per ton of cellulose fiber.

The cellulosic fibers may have been treated with a debonding agent prior to treatment with the crosslinking agent. Debonding agents tend to minimize interfiber bonds and allow the fibers to separated from each other more easily. The debonding agent may be cationic, non-ionic or anionic. Cationic debonding agents appear to be superior to non-ionic or anionic debonding agents. The debonding agent typically is added to cellulose fiber stock.

Suitable cationic debonding agents include quaternary ammonium salts. These salts typically have one or two lower alkyl substituents and one or two substituents that are or contain fatty, relatively long chain hydrocarbon. Non-ionic debonding agents typically comprise reaction products of fatty-aliphatic alcohols, fatty-alkyl phenols and fatty-aromatic and aliphatic acids that are reacted with ethylene oxide, propylene oxide or mixtures of these two materials.

Examples of debonding agents may be found in Hervey et al U.S. Pat. Nos. 3,395,708 and 3,544,862, Emanuelsson et al U.S. Pat. No. 4,144,122, Forssblad et al U.S. Pat. No. 3,677,886, Osborne III U.S. Pat. No. 4,351,699, Hellston et al U.S. Pat. No. 4,476,323 and Laursen U.S. Pat. No. 4,303,471 all of which are in their entirety incorporated herein by reference. A suitable debonding agent is Berocell 584 from Berol Chemicals, Incorporated of Metairie, La. It may be used at a level of 0.25% weight of debonder to weight of fiber. Again, a debonding agent may not be required.

A high-bulk fiber is available from Weyerhaeuser Company. It is HBA fiber and is available in a number of grades. The suitability of any of the grades will depend upon the end product being manufactured. Some may be more suitable for food grade applications than others. U.S. patent application Ser. Nos. 07/395,208 which issued as U.S. Pat. No. 5,225,047 on Jul. 6, 1993 and 07/607,268, a continuation of which issued as U.S. Pat. No. 5,324,391 on Jun. 28, 1994, describe a method and apparatus for manufacturing HBA fibers. These applications are in their entirety incorporated herein by reference.

In essence, a conveyor 12 (FIG. 1) transports a cellulose fiber mat 14 through a fiber treatment zone 16 where an applicator 18 applies a crosslinking agent onto the mat 14. Typically, chemicals are applied uniformly to both sides of the mat. The mat 14 is separated into substantially unbroken individual fibers by a fiberizer 20. Hammermills and disc refiners may be used for fiberization. The fibers are then dried and the crosslinking agent cured in a drying apparatus 22.

The high bulk fibers produce cellulosic products having poor fiber-to-fiber bond strength. One of the ways of measuring fiber-to-fiber bond strength is tensile index. Tensile index is a measure of a sheet's tensile strength normalized with respect to the basis weight of the sheet and provides a measure of the inherent tensile strength of the material. A wet laid sheet made from the unmodified and unbeaten cellulose fibers from which the HBA is subsequently made has a tensile index of about 1.1 Nm/g whereas a similar wet laid sheet made from the chemically crosslinked high-bulk fibers have a tensile index of only about 0.008 Nm/g, a 140 fold decrease. Fibers can readily be removed from pads of the high-bulk material simply by blowing air across the pad.

The composition of the present invention requires a water-borne binding agent. The binding agent may be an anionic, non-ionic, or cationic type. This produces a product that has increased bulk, decreased density, and strength that is substantially the same as products made without high bulk fiber. The term water-borne means any binding agent capable of being carried in water and includes binding agents that are soluble in, dispersible in or form a suspension in water. Suitable water-borne binding agents include starch, modified starch, polyvinyl alcohol, polyvinyl acetate, polyethylene/acrylic acid copolymer, acrylic acid polymers, polyacrylate, polyacrylamide, polyamine, guar gum, oxidized polyethylene, polyvinyl chloride, polyvinyl chloride/acrylic acid copolymers, acrylonitrile/butadiene/styrene copolymers and polyacrylonitrile. Many of these will be formed into latex polymers for dispersion or suspension in water. Particularly suitable binding agents include starches, polyvinyl alcohol and polyvinyl acetate. The purpose of the binding agent is to increase the overall binding of the high-bulk fiber within the sheet.

Various amounts of the water-borne binding agent may be used. The amount of binding agent used may expressed as a loading level. This is the amount of binding agent relative to the dry weight of the fiber and binding agent. Suitable binding agent loading levels are from about 0.1 weight percent to about 6 weight percent, preferably from about 2.0 weight percent to about 5.0 weight percent and most preferably from about 2.5 weight percent to about 4.5 weight percent.

In one embodiment of the invention the binding agent may be applied to the high-bulk fiber pad and sucked through the sheet by vacuum. The excess binding agent is removed, as by blotting. The sheets are further dried by drawing 140° C. air through the pads. Alternatively, the pads may be wet formed by conventional means and the binding agent added to the water in which the fibers are suspended.

The treated pads have low density and good stiffness. The pads can be cut easily using a sharp knife. The material strongly resembles expanded polystyrene in appearance and feel.

The material, either alone or mixed with conventional fiber may be used as single ply folding boxboard and used in the formation of folding paperboard boxes.

The use of up to 20% high bulk additive fibers by weight of the total fibers in the paperboard can speed up the forming, pressing and drying process and improve calendering in the manufacture of the paperboard depending on what the limiting steps of the process are.

EXAMPLE 1

Twenty grams of commercially available HBA fiber were dispersed in 9.5 liters of water to form an HBA/water slurry having a consistency of 0.21%. Consistency is the weight of air-dry pulp as a percentage of the pulp/water slurry weight. The slurry was placed in an 8"×8" laboratory hand-sheet mold. The slurry was dewatered to form a pad, first by suction, then by hand pressing between blotting papers, and finally by drying in an oven at a temperature of 105° C. The resulting cellulosic pad had a density of 0.02 g/cm$^3$, a bulk of 50 cm$^3$/g. The density of commercially available paper typically is in the range of from about 0.5 g/cm$^3$ to about 1 g/cm$^3$, a bulk of from about 2 cm$^3$/g to 1 cm$^3$/g. The density of wet-laid HBA fiber pads is about 25 to 50 times lower than the densities of typical paper sheets, and the bulk is about 50 to 100 times greater than the bulk of typical paper sheets. Fibers could be removed from the HBA fiber pad by blowing air across the sheet.

EXAMPLE 2

6.5 grams of HBA fiber were dispersed in eight liters of water to provide a cellulose-water slurry having a consistency of about 0.08%. The slurry was formed into pads in a six-inch diameter laboratory hand sheet mold. The slurry was dewatered as in Example 2. The resulting pad had a density of 0.025 g/cm$^3$, a bulk of 40 cm$^3$/g.

Tensile indexes for this pad were determined. Tensile indexes for the HBA fiber pad and for a control pad made from NB316, a starting pulp for a commercially available HBA. The results are in Table I.

TABLE I

| Pulp Type | Tensile Index (Nm/g) |
| --- | --- |
| HBA fiber | 0.0081 |
| NB316 control | 1.15 |

Pads of HBA fiber made by air-laying have a similar low tensile index.

High-bulk additive sheets were prepared as in Example 1. Aqueous solutions of water borne binding agents were applied to the sheets. The solution typically is vacuum-sucked through the sheet. Excess binding-agent solution is removed from the sheets first by blotting. The sheets are further dried by drawing air through the pads. The air is at a temperature of about 140° C.

Dry pads made using this process have low density and good stiffness. The strength of the sheets was markedly increased relative to high-bulk additive sheets made without the binding agents. The products could be cut easily with a knife. The material strongly resembles expanded polystyrene in appearance and feel.

EXAMPLE 3

Six-inch diameter pads were formed from high-bulk additive fibers using either an air-laid or a wet-laid process. Either process forms essentially unbonded high-bulk additive pads. The pads were weighed and placed in a six-inch diameter Buchner funnel.

The pads were saturated with aqueous solutions of either starch or polyvinyl alcohol. The starch was HAMACO 277 starch from A. E. Staley Manufacturing Company. This is an essentially non-ionic or neutral charge starch. The polyvinyl alcohol was ELVANOL HV from DuPont Chemical Company. The amounts of binding agent in the solutions ranged from about 0.5 weight % to 5 weight % of the total weight of the solution.

The pads were removed from the Buchner funnel and supported between sheets of synthetic nonwoven. A suitable nonwoven is James River 0.5 oz/yd$^2$ Cerex 23 nonwoven. The supported pad was squeezed between blotting papers to remove excess liquid from the saturated sheets. The pads were then dried by passing hot air, at about 140° C., through the pads using a laboratory thermobonder. Binder loading levels of from about 2.5 to about 5% of the weight of the fiber in the pad have been obtained using this process. Binder loading levels typically are about 3 to about 4.5% of the weight of the fiber in the pad.

Pulp densities and tensile indexes were determined as in Example 2. NB316 with and without binder and HBA fibers without binder were used as controls. The samples and results are given in Table II. It will be noted that most of the binder treated HBA fiber pads have a tensile index equal to or greater than the 1.15 Nm/g tensile index of NB316 without binder even though the densities of the HBA pads were less than one-half the 0.220 g/cm$^3$ density of the NB316 pad. It was noted that polyvinyl alcohol greatly increased the tensile index of HBA fiber pads. Polyvinyl alcohol bonded HBA fiber pads had a density of one-third that of starch bonded NB316 fibers but had a tensile index that almost equaled that of the starch bonded NB316. The density of another sample of polyvinyl alcohol bonded HBA fiber pads was less than one-half the density of the starch bonded NB316 but its tensile index was more than twice that of the starch bonded NB316.

FIG. 2 is an electron-microscope micrograph of an HBA/water borne binding agent composition produced according to Example 3. FIG. 2 shows that the water-borne binding agent substantially completely collects at the crossover or contact points between fibers where it is seen as a bridge between them. Without limiting the invention to one theory of operation, it is believed that the polymer collects or concentrates at the crossover or contact points primarily by capillary action. The majority of the binding agent is located where it is needed.

EXAMPLE 4

Six-inch diameter air-laid HBA fiber pads were weighed and placed in a six-inch diameter Buchner funnel. Aqueous solutions were prepared of a polyvinyl acetate latex polymer, Reichold PVAc latex 40–800, at concentrations of polymer of 2% and 5% of the total weight of the solution. The solutions were passed through the pads in the funnels. The pads were dried in the same manner as the pads in Example 4. The loading levels of the polymeric binder were from about 2 weight % to about 4 weight %. The resultant pads were well bonded.

EXAMPLE 5

9.95 grams of a 10/90 weight ratio blend of chemically crosslinked high-bulk fiber and NB316 conventional pulp were dispersed in 9.5 liters of water. The water contained 0.8 weight % water-soluble cationic potato starch, D.S. 0.3 "ACCOSIZE 80" starch. The cellulosic dispersion was placed in an 8"×8" hand-sheet mold to produce a pad having a basis-weight of about 240 g/m$^2$. Excess moisture was removed from the pad by pressing between blotter papers, and the pad was dried in a fan oven at 105° C.

The dry pad was tested for density, taber stiffness and thermal resistance. The same values were obtained for

TABLE II

| Fiber Type | Bonding Agent | Solution Strength % of Solution Weight | Loading Level % of Pulp Weight | Pad Density g/cm$^3$ | Pad Bulk cm$^3$/g | Tensile Index Nm/g |
|---|---|---|---|---|---|---|
| NB316 wet laid | None | N/A | N/A | 0.220 | 4.55 | 1.15 |
| NB316 wet laid | Starch HAMACO 277 | 2 | 7.5 | 0.240 | 4.17 | 1.92 |
| HBA wet laid | None | N/A | N/A | 0.025 | 40 | 0.0081 |
| HBA air laid | Starch HAMACO 277 | 5 | 4.1 | 0.108 | 9.26 | 1.504 |
| HBA air laid | Starch HAMACO 277 | 2 | 3.8 | 0.073 | 13.7 | 1.127 |
| HBA air laid | Starch HAMACO 277 | 0.5 | 3.2 | 0.043 | 23.26 | 0.413 |
| HBA air laid | Polyvinyl alcohol Elvanol 52-22 | 5 | 2.9 | 0.077 | 12.99 | 1.82 |
| HBA air laid | Polyvinyl alcohol Elvanol HV | 5 | 3.8 | 0.100 | 10 | 4.71 |
| 25% HBA/75% NB316 blend by weight - air laid | Starch HAMACO 277 | 2 | 4.4 | 0.106 | 9.43 | 1.189 |

It can also be seen in Table II that a starch bonded blend of HBA fibers and conventional pulp fibers can provide a product that has a low density and a tensile index that is almost the same as conventional pulp fiber alone.

expanded polystyrene from the lid of a clam-shell packaging box used by McDonald's Corporation. The cost of material per unit area in the cellulosic pad and in the polystyrene lid were substantially equal. The results of the tests are given in Table III.

TABLE III

| Material | Basis Weight, g | Caliper, mm | Density, g/cm$^3$ | Bulk, cm$^3$/g | Starch Loading, % Weight on Fiber | Taber Stiffness, (sd) | Thermal Resistance, mK/W |
|---|---|---|---|---|---|---|---|
| Blend, 10% HBA/ 90% NB316 by weight | 240 | 1.5 | 0.16 | 6.25 | 3.2 | 123 (10) | 0.049 |
| Styrofoam | 120 | 1.0 | 0.12 | 8.33 | N/A | 88–128* | 0.035 |

*stiffness of styrofoam varies with the direction relative to the forming process.

The fiber blend compared favorably with the styrofoam material.

EXAMPLE 6

The cellulosic-fiber/bonding agent composition can be used to form molded products which have characteristics that are similar to molded styrofoam. They can be used for, among other things, food product containers.

Figure 3B:
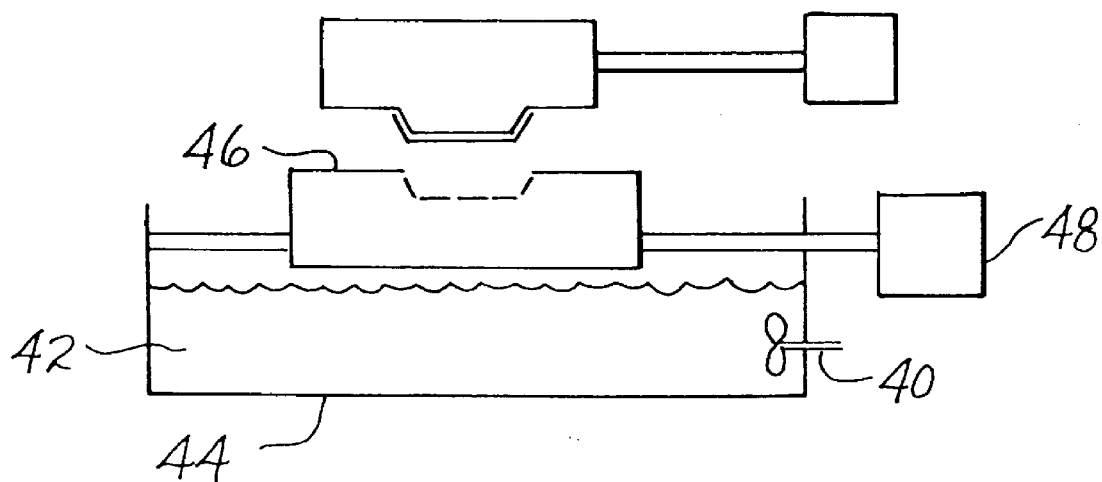

The fiber/bonding agent composition was used to form a molded plate. A 90/10 weight percent fiber blend of 2708.5 g. of conventional bleached southern pine kraft fluff pulp (NB316) and 300.5 g of individualized chemically crosslinked fiber (HBA) were slurried in 433 liters of water. The water contained 1% by weight polyvinyl alcohol, DuPont Elvanol HV. 50 ppm of an anti-foaming agent, Cynol 420, was added to the slurry to prevent froth build-up. The slurry was formed into 10" diameter dinner plates using an Emery International plate forming machine. In this machine, FIG. 3, a pulp agitator 40 continuously agitates the pulp slurry 42 in a slurry tank 44. A porous, shaped wire forming screen 46 was immersed in the pulp slurry and water was moved from the screen by a dewatering pump 48. The screen is removed from the slurry when a sufficient amount of pulp 50 is on the screen 46. The pulp plate 50 is transferred to a transfer mold 52 and held by the vacuum formed by the vacuum pump 54. The plate 50 is removed from the mold 52 and dried in an oven.

The thermal resistance of the resulting plates was high. The resulting plates had a density of about 0.16 g/cm$^3$ as compared with a density of 0.25 to 0.5 g/cm$^3$ for conventional molded pulp articles made from recycled pulp fiber.

EXAMPLE 7

Figure 5:
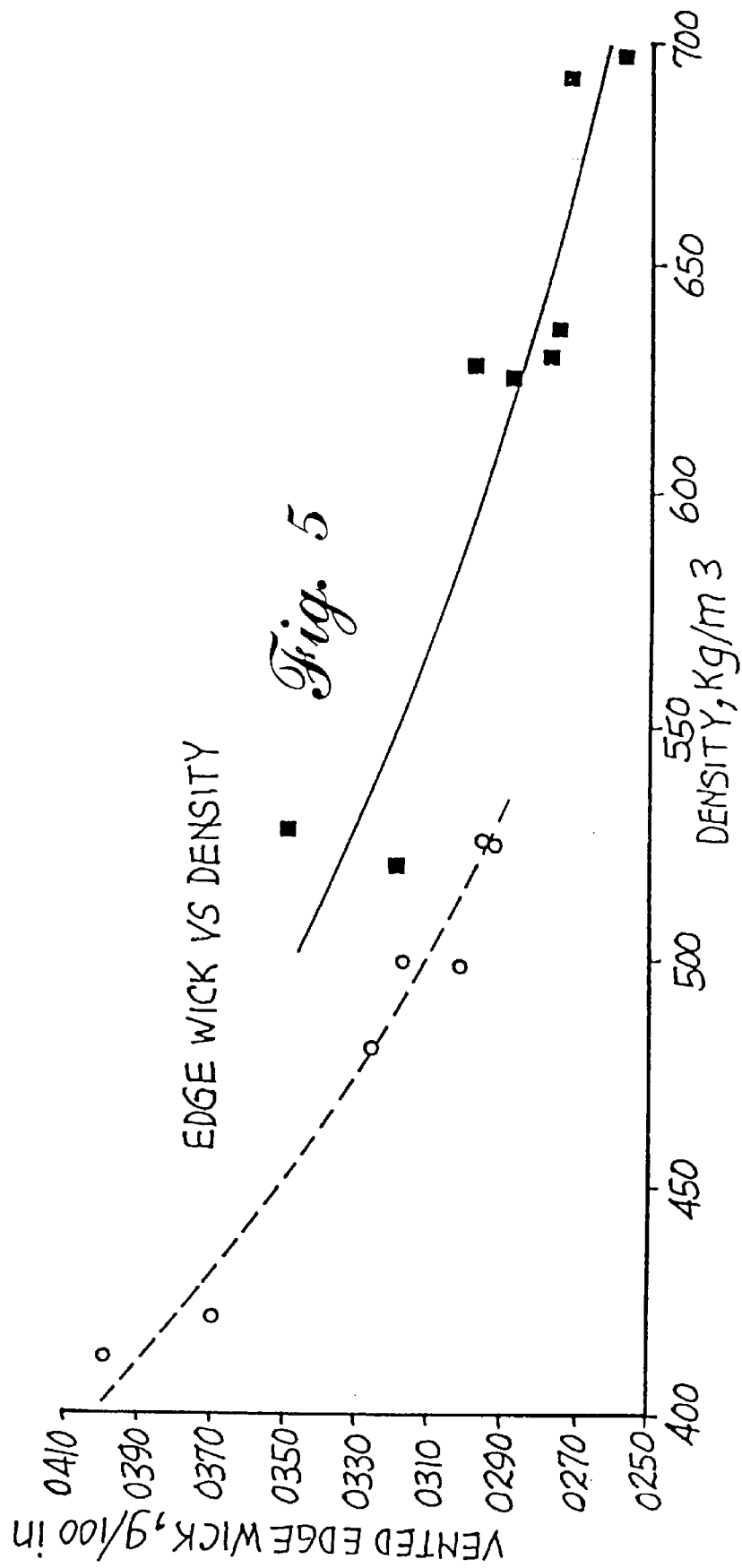
FIG. 5 is a graph of edge wicking vs. density and shows the decrease in absorbency when high bulk fibers are included in the furnish.

The edge wicking of sheets of conventional fibers and sheets of a mixture of conventional fibers and high bulk additive fibers were compared. Tappi hand sheets were prepared. They contained 10 pounds of starch per air dry ton of fiber and 5 pounds of Kymene per air dry ton of fiber. Kymene is a registered trademark of Hercules, Inc., Wilmington Del., for a cationic polyamide-epichlorohydrin resin used in paper making. Two fiber furnishes were used. The first furnish contained conventional pulp fiber. The second contained 90% by weight conventional pulp fiber and 10% by weight high bulk additive fiber. The wet hand sheets were pressed to different densities and compared for edge wicking. The sheets were weighed and the edges of the sheets placed in a liquid for a specified period of time. The sheets were weighed again. Wicking is expressed as grams of liquid absorbed per 100 inches of edge. The results are shown in FIG. 5. At a given density the conventional fiber absorbed more liquid than the conventional fiber/high bulk additive fiber mixture.

EXAMPLE 8

Figure 4:
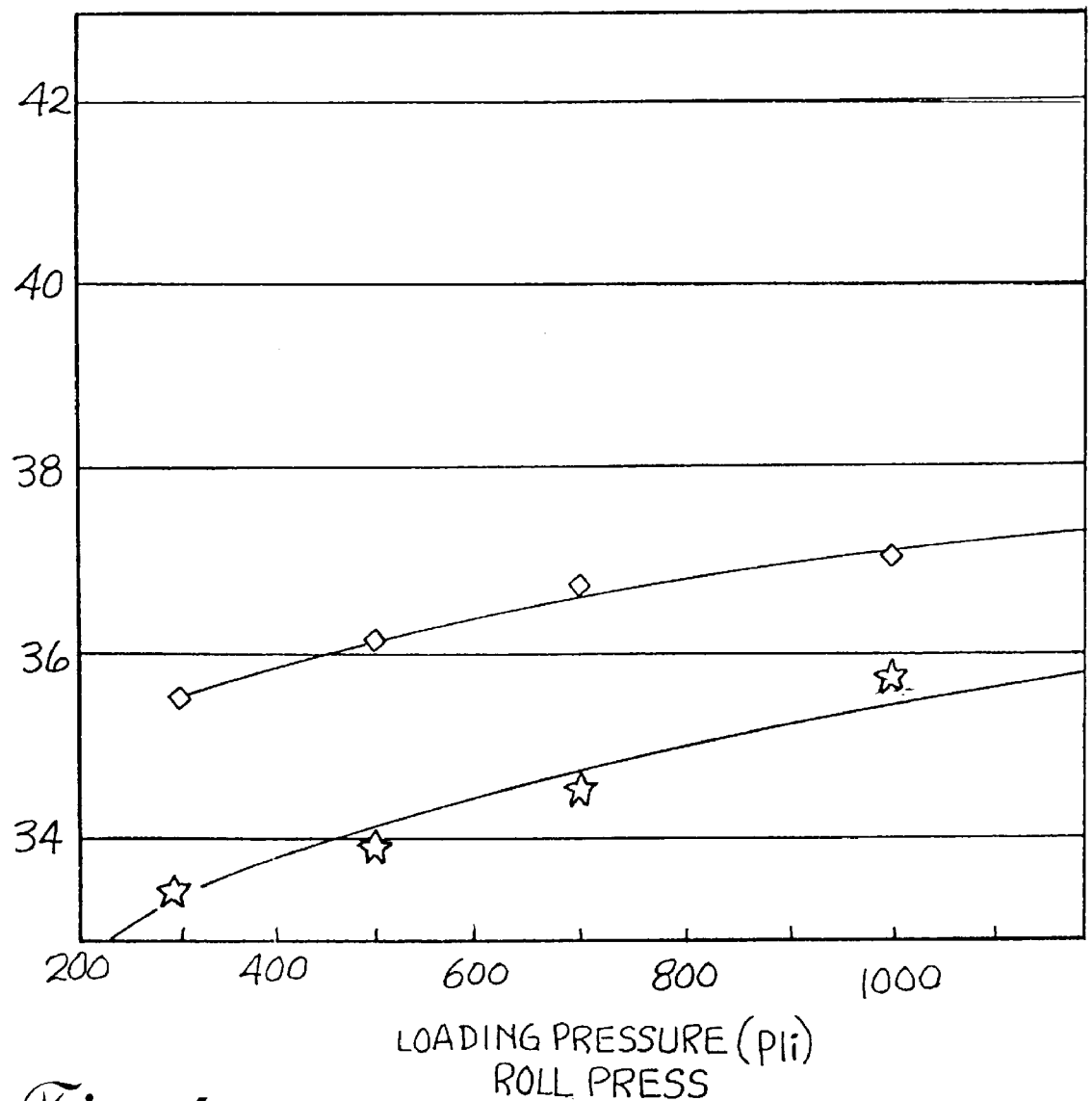
FIG. 4 is a graph of press solids vs. loading pressure and shows the increase in productivity possible when high bulk fibers are included in the furnish.

The solids level of sheets of conventional fibers and a mixture of conventional fibers and high bulk additive fibers after wet pressing were compared. Two pulp furnishes were used. The first pulp contained conventional pulp fiber. The second contained 90% by weight conventional pulp fiber and 10% by weight high bulk additive fiber. Wet hand sheets were roll pressed at different loading pressures and the solids levels in the sheets after pressing were determined on a weight percent. The results are shown in FIG. 4. The sheets of a mixture of conventional fibers and high bulk additive fibers had a higher solids level, i.e., they were drier after pressing than the conventional fiber sheets. The conventional fiber is shown in a bold line and the conventional fiber/high bulk additive mixture is shown in dotted lines.

EXAMPLE 9

Single ply handsheets were made on an 8"×8" former equipped with a process water recycling facility. The pulps used were bleached kraft Douglas-fir and the HBA described earlier. The HBA was used without beating but prior to use was given 30 seconds of defibration in a Waring blender (0.2% consistency in water) to remove any tight fiber bundles.

Where starch was added, the process water was recirculated to enable a number of handsheets to be made from each batch of starch. The starch was "Acosize 80" cationic starch, Raison Inc, PA. It was cooked first at 4% solids and then diluted to the desired level in the process water. solids starch refers to the level of starch dissolved in the process water and not to the loading in the sheet.

The handsheets were dried on a lab "steam can" dryer. There was no calendering. The results are given in Table IV. The addition of the binding agent improves the stiffness of the HBA sheets.

Reference to FIGS. 6–9 will show clearly how the binder of the present invention locates at the fiber—fiber crossover points between two crosslinked HBA fibers or HBA fibers and other more conventional cellulose fibers. FIG. 6 is a scanning electron Micrograph (SEM) of a sheet made using refined conventional Douglas-fir kraft fiber but without any binder. Surface fibrils loosened during refining are clearly seen bridging adjacent fibers to which they are held by hydrogen bonding. This sheet corresponds to Samples 1a or 1b and 2a or 2b of Table IV. FIG. 7 shows a similarly made sheet with the difference that about 1% cationic starch, based on water in the fiber slurry, was added to the pulp slurry prior to forming. The starch is seen on the surface of the fibers but bonding is again primarily through fibrils spanning fiber-to-fiber and held by hydrogen bonds.

FIG. 8 shows the bond between a crosslinked HBA fiber and conventional Douglas-fir fiber in a sheet formed according to Sample 4 of Table IV. The HBA fiber is the upper fiber with the relatively smooth surface while the Douglas-fir fiber is seen coming in from the lower left. Between them at the crossover point is a globule of starch which serves to bind the unfibrillated HBA fiber to the Douglas-fir fiber. FIG. 9 represents a similar situation as seen in partial cross section. The upper fiber of approximately circular cross section is the HBA fiber. A collapsed Douglas-fir fiber is seen at the lower left. A globule of starch binder is plainly seen between them. It is surprising and unexpected that the cationic starch additive would be localized in the manner seen.

As is seen from the examples, the invention encompasses sheets or pad like structures which may range between densities as high as about 0.7 g/cm$^3$ and as low as about 0.02 g/cm$^3$. These correspond to bulk factors between about 1.4 cm$^3$/g and 50 cm$^3$/g. A preferred range of densities is below about 0.6 g/cm$^3$ corresponding to bulk factors greater than about 1.7 cm$^3$/g.

It will be apparent to those skilled in the art that the specification and examples are exemplary only and the scope of the invention is embodied in the following claims.

2. The product of claim 1 wherein the water-borne binding agent is anionic, nonionic, or cationic.

3. The product of claim 1 wherein the water-borne binding agent is selected from the group consisting of a starch, a modified starch, a polyvinyl alcohol, a polyvinyl acetate, a polyethylene/acrylic acid copolymer, an acrylic acid polymer, a polyacrylate, a polyacrylamide, a polyamine, guar gum, an oxidized polyethylene, a polyvinyl chloride, a polyvinyl chloride/acrylic acid copolymer, an acrylonitrile/butadiene/styrene copolymer and polyacrylonitrile.

4. The product of claim 3 wherein the binding agent is selected from the group consisting of starch and modified starch.

TABLE IV

Basic Sheet Properties and Taber Stiffness

| Sample # Replicates a and b | Sample Description | Target Basis Wt. (gsm) | Actual Basis Wt. (gsm) | Caliper (cm) ± SD | Density (g/cm$^3$) ± SD | Taber Stiffness (15°) ± SD |
|---|---|---|---|---|---|---|
| 1a | 100% Douglas-fir High Basis Wt. CONTROL | 316 | 312 | 0.057 ± 0.003 | 0.64 ± 0.03 | 151 ± 12 |
| 1b | 100% Douglas-fir High Basis Wt. CONTROL | 316 | 324 | 0.053 ± 0.004 | 0.70 ± 0.04 | 149 ± 18 |
| 2a | 100% Douglas-fir Low Basis Wt. CONTROL | 290 | 293 | 0.050 ± 0.000 | 0.65 ± 0.02 | 126 ± 19 |
| 2b | 100% Douglas-fir Low Basis Wt. CONTROL | 290 | 291 | 0.049 ± 0.004 | 0.67 ± 0.05 | 124 ± 6 |
| 3a | 90% Douglas-fir 10% HBA NO STARCH | 290 | 291 | 0.055 ± 0.004 | 0.56 ± 0.070 | 126 ± 11 |
| 3b | 90% Douglas-fir 10% HBA NO STARCH | 282 | 298 | 0.056 ± 0.004 | 0.57 ± 0.04 | 124 ± 17 |
| 4 | 90% Douglas-fir 10% HBA 1.0% STARCH* | 290 | 293 | 0.059 ± 0.003 | 0.54 ± 0.03 | 152 ± 15 |
| 5 | 90% Douglas-fir 10% HBA 0.41% STARCH | 290 | 283 | 0.057 ± 0.003 | 0.56 ± 0.04 | 148 ± 9 |
| 6 | 90% Douglas-fir 10% HBA 0.18% STARCH | 290 | 282 | 0.059 ± 0.004 | 0.56 ± 0.08 | 136 ± 15 |

*Starch level is solids level of process water

We claim:

1. A fiber-binder sheet or pad product wherein adjacent fibers are in contact and form plural fiber crossover points which comprises:

from 0.5–100.0 weight percent chemically intrafiber crosslinked high bulk cellulosic fibers in admixture with 99.5–0.0 weight percent conventional cellulose fibers; and from about 0.1 to about 6 weight percent of a water borne binding agent, said binding agent being more heavily concentrated at the fiber—fiber crossover points of crosslinked fibers with each other and with other fibers during removal of water from the product, whereby the binder more effectively contributes strength and integrity to the structure.

5. The product of claim 3 wherein the binding agent is polyvinyl alcohol.

6. The product of claim 1 wherein the product comprises from about 0.25 weight percent to about 5 weight percent water-borne binding agent.

7. The product of claim 1 further including from about 5 weight percent to about 99.5 weight percent conventional fiber furnish.

8. The product of claim 1 further including at least about 90 weight percent conventional fiber furnish.

9. The product of claim 1 further including at least about 80 weight percent conventional fiber furnish.

10. The product of claim 1 wherein said high bulk fibers are individualized prior to forming said sheet or pad product.

11. The product of claim 1 in which the density is less than about 0.6 g/cm$^3$ which corresponds to a bulk greater than about 1.7 cm$^3$/g.

* * * * *